(12) United States Patent
Kato et al.

(10) Patent No.: US 6,696,468 B2
(45) Date of Patent: Feb. 24, 2004

(54) (S)-4-AMINO-5-CHLORO-2-METHOXY-N-[1-[1-(2-TETRAHYDROFURYL-CARBONYL)-4-PIPERIDINYLMETHYL]-4-PIPERIDINYL] BENZAMIDE, PROCESS FOR THE PREPARATION THEREOF, PHARMACEUTICAL COMPOSITION CONTAINING THE SAME, AND INTERMEDIATE THEREFOR

(75) Inventors: Shiro Kato, Sakai (JP); Hiroshi Yamazaki, Suita (JP); Yoshimi Hirokawa, Ikoma (JP); Yoko Kan, Suita (JP); Naoyuki Yoshida, Sakai (JP); Kazuo Morikage, Suita (JP); Yukiko Morikage, Suita (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 10/321,615

(22) Filed: Dec. 18, 2002

(65) Prior Publication Data

US 2003/0216433 A1 Nov. 20, 2003

(30) Foreign Application Priority Data

May 16, 2002 (JP) ........................................ 2002-141262

(51) Int. Cl.$^7$ ................... A61K 31/4545; C07D 405/14
(52) U.S. Cl. ........................................ 514/316; 546/182
(58) Field of Search ........................... 514/316; 546/187

(56) References Cited

U.S. PATENT DOCUMENTS 6,294,555 B1    9/2001   Kato et al. ................... 514/316

FOREIGN PATENT DOCUMENTS

| JP | 11-001472   | 1/1999 |
| JP | 2000-80081  | 3/2000 |
| JP | 2001-122784 | 5/2001 |

OTHER PUBLICATIONS

D. Craig et al., "Pharmacological Characterization of a Neuronal Receptor for 5–Hydroxytryptamine in Guinea Pig Ileum with Properties Similar to the 5–Hydroxytryptamine$_4$ Receptor[1]", The Journal of Pharmacology and Experimental Therapeutics, vol. 252, No. 3, pp. 1378–1386, 1990.

N. Yoshida et al., "AS–4370, A New Gastrokinetic Agent, Enhances Upper Gastrointestinal Motor Activity in Conscious Dogs", The Journal of Pharmacology and Experimental Therapeutics, vol. 257, No. 2, pp. 781–787, 1991.

L. Carlsson et al., "Electrophysiological Characterization of the Prokinetic Agents Cisapride and Mosapride in vivo and in vitro: Implications for Proarrhythmic Potential", The Journal of Pharmacology and Experimental Therapeutics, vol. 282, No. 1, pp. 220–227, 1997.

The Journal of Pediatrics, Jan. 1997, p. 164.

Primary Examiner—Patricia L. Morris
(74) Attorney, Agent, or Firm—Wenderoth, Lind & Ponack, L.L.P.

(57) ABSTRACT

(S)-4-Amino-5-chloro-2-methoxy-N-[1-[1-(2-tetrahydrofuryl-carbonyl)-4-piperidinylmethyl]-4-piperidinyl]benzamide of the following formula (I):

(I)

or a pharmaceutically acceptable acid addition salt thereof, or a hydrate thereof, and a process for preparing the same, a pharmaceutical composition containing the same, and intermediate therefor.

The compound of the present invention is useful as a gastrointestinal motility enhancer or a gastrointestinal prokinetic agent, which shows a potent affinity for 5-HT$_4$ receptor, and shows few effects on the heart, and further shows few side effects on the central nervous system based on the dopamine D$_2$ receptor.

4 Claims, No Drawings

(S)-4-AMINO-5-CHLORO-2-METHOXY-N-[1-[1-(2-TETRAHYDROFURYL-CARBONYL)-4-PIPERIDINYLMETHYL]-4-PIPERIDINYL] BENZAMIDE, PROCESS FOR THE PREPARATION THEREOF, PHARMACEUTICAL COMPOSITION CONTAINING THE SAME, AND INTERMEDIATE THEREFOR

TECHNICAL FIELD

The present invention relates to a novel (S)-4-amino-5-chloro-2-methoxy-N-[1-[1-(2-tetrahydrofurylcarbonyl)-4-piperidinylmethyl]-4-piperidinyl]benzamide exhibiting a potent gastrointestinal motility enhancing effect based on its agonistic activity on serotonin 4 receptor (hereinafter, occasionally referred to as $5\text{-}HT_4$ receptor) and having few effects on the heart. Said compound is an amide compound of 4-amino-5-chloro-2-methoxybenzoic acid.

The present invention also relates to a process for the preparation of said compound, a pharmaceutical composition containing said compound, and an intermediate therefor.

BACKGROUND ART

JP-A-2000-80081 discloses that 1-(1-substituted-4-piperidinyl-methyl)-4-piperidinylbenzamide and an ester derivative thereof of the following formula (P-1), which is formed by binding a 1-(1-substituted-4-piperidinylmethyl)-4-amino(or hydroxy)-piperidine derivative with a 4-amino-5-halogeno-2-alkoxybenzoic acid via an amide or ester bond, have selective agonistic effects on $5\text{-}HT_4$ receptor, and are useful as a medicament in the prophylaxis or treatment of various gastrointestinal diseases, etc.

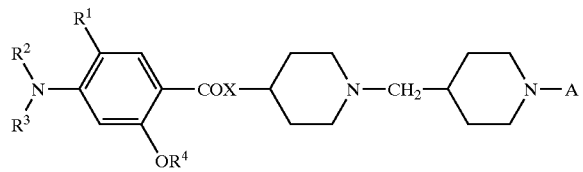

(P-1)

wherein R' is a halogen atom;
$R^2$ is a hydrogen atom or a lower alkyl group;
$R^3$ is a hydrogen atom, a lower alkyl group, etc.;
$R^4$ is a hydrogen atom or a lower alkyl group;
X is —NH— or —O—;
A is a group of the following formula (A-1), (A-2) or (A-3):

 (A-1)

(in which p is 0, 1, 2, 3, 4 or 5,
$R^7$ is a hydrogen atom, a lower alkyl group, etc.,
$R^8$ is a hydrogen atom or a lower alkyl group,
$R^9$ is a lower alkoxy group, etc.),

—CO—$R^{10}$ (A-2)

(in which $R^{10}$ is a substituted or unsubstituted phenyl-lower alkyl group, a substituted or unsubstituted heteroaryl group, a saturated monocyclic or bicyclic hetero ring, a cycloalkyl group, a lower alkenyl group, a trifluoromethyl group, a lower alkyl group being substituted by a heteroaryl group, etc.),

 (A-3)

(in which q is 0, 1, 2, 3 or 4,
Z is —$CH_2$— or —O—,
$R^{11}$ is a hydrogen atom, a lower alkyl group, a cycloalkyl group, etc., provided that (1) when q is 0, then Z is —$CH_2$—, etc.).

The above patent publication also discloses the compound of Example 5 of the following formula (Compound A) as a compound of the formula (P-1) wherein $R^{10}$ in the above formula (A-2) is a saturated monocyclic hetero ring containing an oxygen atom.

Compound A

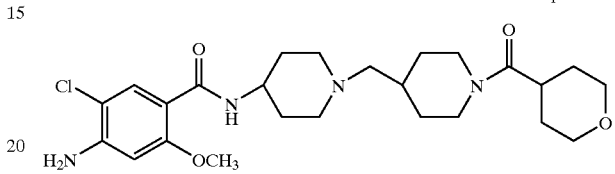

In addition, the above patent publication discloses the compound of Example 19 of the following formula (Compound B) as a compound of the formula (P-1) wherein $R^{10}$ in the formula (A-2) is a heteroaryl group containing an oxygen atom.

Compound B

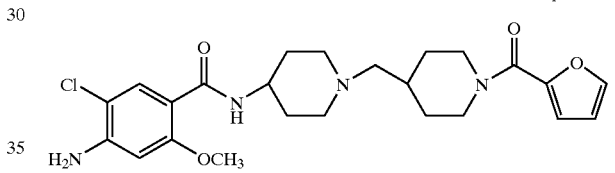

However, the above patent publication never concretely discloses the compound of the present invention of the formula (I) as disclosed below in the form of an (S)-optical isomer, which corresponds to compounds of the formula (P-1) wherein R'" in the above formula (A-2) is a 2-tetrahydrofuryl group.

In the 1990s, $5\text{-}HT_4$ receptor was found during the studies on 5-HT receptor subtypes being participated in gastrointestinal motility enhancing effect by metoclopramide and cisapride, and it was confirmed that said benzamide derivatives enhance the gastrointestinal motility by activating $5\text{-}HT_4$ receptor being widely distributed throughout the gastrointestinal organs (cf., J. Pharmacol. Exp. Ther., 252, 1378–1386 (1990); J. Pharmacol. Exp. Ther., 257, 781–787 (1991)). Thus, a compound activating $5\text{-}HT_4$ receptor may be expected to enhance the gastrointestinal motility, but metoclopramide as mentioned above shows the central nervous system depression based on the antagonistic activity on dopamine $D_2$ receptor, and cisapride was observed to show disadvantageous effects on the heart, and hence, it is difficult to use these medicaments in the clinical field [cf., J. Pharmacol. Exp. Ther., 282, 220–227 (1997); The Journal of Pediatrics, January. 164 (1997)].

Besides, recently, there has been a growing tendency of increase in the number of patients being suffering from symptoms associated with gastrointestinal motility disorders due to the complicated society and aging society, and under these circumstances, it has been strongly desired to develop an excellent gastrointestinal motility enhancer (gastrointestinal prokinetic agent) with less adverse effects.

DISCLOSURE OF INVENTION

Under these circumstances, the present inventors have intensively studied on 1-(1-substituted-4-piperidinylmethyl)-4-piperidine derivatives activating 5-HT$_4$ receptor, and have found that 1-(1-substituted-4-piperidinylmethyl)-4-piperidinylamide or a corresponding ester derivative thereof, which is bound with a 4-amino-5-halogeno-2-alkoxybenzoic acid or a 4-amino-5-halogeno-2,3-dihydro-benzo[b]furan-7-carboxylic acid respectively via an amide or ester bond, shows a potent agonistic activity on 5-HT$_4$ receptor, and is useful as an excellent gastrointestinal motility enhancer, and they filed a patent application as to the compounds of the above-mentioned formula (P-1) (i.e., the above patent publication JP-A-2000–80081).

Although it is apparent that medicaments belonging to this kind of category exhibit sufficient gastrointestinal motility enhancing activity, but it has strongly been desired to develop medicaments having no disadvantageous effects on the heart, particularly, no action of prolonging QT interval of electrocardiogram, which is a serious clinical problem of a gastrointestinal motility enhancer, cisapride as mentioned above, and having no central nervous system depression based on the dopamine D$_2$ receptor antagonistic activity as observed in metoclopramide, and it has become a new big issue to solve these problems.

Under these circumstances, in order to find out a safer benzoic acid derivative, which exhibits an excellent enhancing activity on the digestive tract with few effects on the heart, etc. as few as possible and further show no antagonistic effects on dopamine D$_2$ receptor, the present inventors synthesized various derivatives and studied on the pharmacological activities thereof.

Aiming at the compounds of the formula (P-1) wherein a saturated monocyclic hetero ring bonds to the carbonyl group as a substituent A, the present inventors have tried to convert the substituents into various ones wherein a hetero atom does not directly bond to the carbonyl group, they have finally found that only a compound of the formula (P-1) wherein the substituent A is a specific substituent binding to the carbonyl group at the 2-position of the tetrahydrofuran ring, i.e., 4-amino-5-chloro-2-methoxy-N-[1-[1-(2-tetrahydrofurylcarbonyl)-4-piperidinylmethyl]-4-piperidinyl]benzamide, maintains a potent agonistic activity on 5-HT$_4$ receptor and a potent inducing activity of defecation by oral administration thereof, and further said compound has high safety with extremely weak effects on the heart. 4-Amino-5-chloro-2-methoxy-N-[1-[1-(2-tetrahydrofuryl-carbonyl)-4-piperidinylmethyl]-4-piperidinyl]benzamide thus newly found has an asymmetric carbon atom at the 2-position of the tetrahydrofuryl ring. Then, the present inventors separated said compound to an (S)-isomer and an (R)-isomer, and tried various pharmacological tests thereon. As a result, they have found that these optical isomers showed pharmacological activities such as a 5-HT$_4$ receptor agonistic activity and an inducing activity of defecation as almost equal to the racemic compound thereof, and further that these optical isomers showed few effects on the heart. In addition, the present inventors tested on these optical isomers with respect to their binding activities to various receptors, and they have unexpectedly found that only one of these optional isomers, (S)-4-amino-5-chloro-2-methoxy-N-[1-[1-(2-tetrahydrofurylcarbonyl)-4-piperidinylmethyl]-4-piperidinyl]benzamide, is a selective 5-HT$_4$ receptor agonist having no inhibitory activity of dopamine D$_2$, which can be a cause for side effects on the central nervous system, and finally have accomplished the present invention.

An object of the present invention is to provide a novel 4-amino-5-chloro-2-methoxy-N-[1-[1-(2-tetrahydrofurylcarbonyl)-4-piperidinyl-methyl]-4-piperidinyl]benzamide exhibiting a potent agonistic activity on 5-HT$_4$ receptor. Another object of the present invention is to provide a compound being useful as a gastrointestinal motility enhancer or a gastrointestinal prokinetic agent. Further object of the present invention is to provide a pharmaceutical composition containing said compound. Still, further object of the present invention is to provide an intermediate for preparing said compound. These and other objects and advantages of the present invention are obvious to any person skilled in the art from the following disclosure.

The present invention provides a 4-amino-5-chloro-2-methoxy-N-[1-[1-(2-tetrahydrofurylcarbonyl)-4-piperidinylmethyl]-4-piperidinyl]-benzamide of the following formula (I), a pharmaceutically acceptable acid addition salt thereof, and a hydrate thereof,

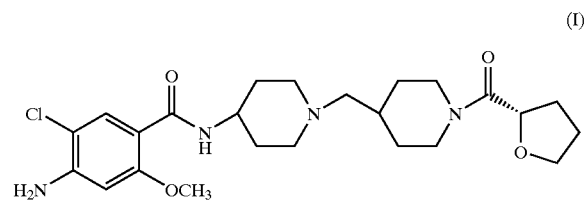

(I)

and a pharmaceutical composition containing the same, and as an intermediate for preparing the above compound (I), a 4-amino-1-[1-(2-tetrahydrofurylcarbonyl)-4-piperidinylmethyl]piperidine of the following formula (V), and an acid addition salt thereof.

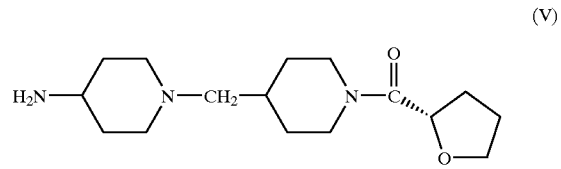

(V)

The pharmaceutically acceptable acid addition salt of the compound of the formula (I) includes a salt with an inorganic acid such as hydrochloride, hydrobromide, hydroiodide, sulfate, phosphate, etc., or a salt with an organic acid such as oxalate, maleate, fumarate, lactate, malate, citrate, tartrate, benzoate, methanesulfonate, succinate, etc.

The acid addition salt of the compound of the formula (V) may be the same pharmaceutically acceptable acid addition salts as mentioned above, but may be any other acid addition salt which can be formed with the compound (V).

The compound of the formula (I) and a pharmaceutically acceptable acid addition salt thereof, and the compound of the formula (V) and an acid addition salt thereof may exist in the form of a hydrate or a solvate, and the present invention also includes these hydrates and/or solvates as well.

The compound of the present invention may be prepared, for example, by the following processes.

Process (a)

The compound of the formula (I) may be prepared by reacting a compound of the formula (II):

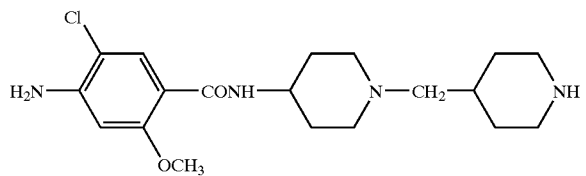

(II)

with a compound of the following formula (III):

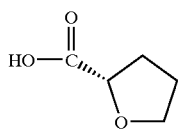

(III)

(Chemical name: (S)-tetrahydrofuran-2-carboxylic acid) or a reactive derivative thereof.

The reactive derivative of the compound (III) includes, for example, a lower alkyl ester (especially, a methyl ester), an active ester, an acid anhydride, and an acid halide (especially, an acid chloride). The active ester includes, for example, p-nitrophenyl ester, pentachloro-phenyl ester, pentafluorophenyl ester, N-hydroxysuccinimide ester, N-hydroxyphthalimide ester, 1-hydroxybenzotriazole ester, 8-hydroxy-quinoline ester, and 2-hydroxyphenyl ester. The acid anhydride includes, for example, a symmetric acid anhydride and a mixed acid anhydride. The mixed acid anhydride includes, for example, a mixed acid anhydride with an alkyl chlorocarbonate such as ethyl chloro-carbonate and isobutyl chlorocarbonate, a mixed acid anhydride with an aralkyl chlorocarbonate such as benzyl chlorocarbonate, a mixed acid anhydride with an aryl chlorocarbonate such as phenyl chloro-carbonate, and a mixed acid anhydride with an alkanoic acid such as isovaleric acid and pivalic acid.

When the compound (III) per se is used, the reaction can be carried out in the presence of a condensing agent such as 1,3-dicyclo-hexylcarbodiimide, 1-ethyl-3-(3-dimethylaminopropyl)carbodiimide hydrochloride, N,N'-carbonyldiimidazole, benzotriazol-1-yloxy-tris-(dimethylamino)phosphonium.hexafluorophosphate, N,N'-disuccin-imidyl carbonate, 1-ethoxycarbonyl-2-ethoxy-1,2-dihydroquinoline, diphenylphosphoryl azide, and propanephosphonic anhydride. When 1,3-dicyclohexylcarbodiimide or 1-ethyl-3-(3-dimethylaminopropyl)-carbodiimide hydrochloride is used as a condensing agent, N-hydroxy-succinimide, 1-hydroxybenzotriazole, 3-hydroxy-1,2,3-benzotriazin-4 (3H)-one, or N-hydroxy-5-norbornen-2,3-dicarboximide, etc. may be added into the reaction system.

The reaction of the compound (III) or a reactive derivative thereof with the compound (II) is carried out in a solvent or without a solvent. The solvent should be selected according to the kinds of the reactive derivative of compound (III), etc., and includes, for example, aromatic hydrocarbons (e.g., benzene, toluene, xylene, etc.), ethers (e.g., diethyl ether, tetrahydrofuran, dioxane, etc.), halogenated hydrocarbons (e.g., methylene chloride, chloroform, etc.), ketones (e.g., acetone, methyl ethyl ketone, etc.), ethyl acetate, acetonitrile, dimethylformamide, dimethyl sulfoxide, 1-methyl-2-pyrrolidone, and these solvents are used alone or in a mixture of two or more solvents.

The reaction may optionally be carried out in the presence of a base, if necessary. The base includes, for example, an alkali metal hydroxide (e.g., sodium hydroxide, potassium hydroxide), an alkali metal carbonate (e.g., sodium carbonate, potassium carbonate), an alkali metal hydrogen carbonate (e.g., sodium hydrogen carbonate, potassium hydrogen carbonate), and organic bases (e.g., triethylamine, tributylamine, diisopropylethylamine, N-methylmorpholine), but an excess amount of the compound (II) may be used instead of a base.

The reaction temperature varies according to the kinds of the reactive derivative of compound (III), etc. to be used, but it is usually in the range of about −30° C. to about 250° C., preferably in the range of about −10° C. to about 150° C.

The compound of the formula (II) may be prepared by the method disclosed in JP-A-2000–80081, and the compound of the formula (III), i.e., (S)-tetrahydrofuran-2-carboxylic acid, is commercially available or may be prepared by a conventional method.

Process (b)

The compound of the formula (I) may be prepared by reacting a compound of the formula (IV):

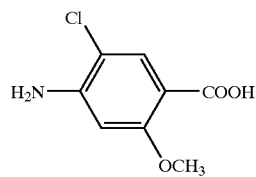

(IV)

or a reactive derivative thereof with a compound of the following formula (V):

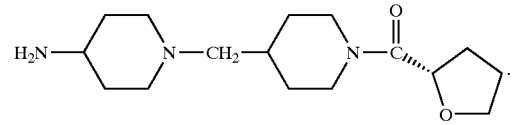

(V)

The reaction of the compound (IV) or a reactive derivative thereof with the compound (V) is carried out in a solvent or without a solvent.

The reactive derivative of the compound (IV) is the same lower alkyl esters, active esters, acid anhydrides, and acid halides as described in the above Process (a). When the compound (IV) per se is used, the reaction can be carried out in the presence of the same condensing agent as disclosed in the above Process (a). The solvent to be used may be the same ones as disclosed in the above Process (a), and should be selected according to the kinds of the reactive derivative of compound (IV), etc. to be used. The reaction is carried out in the presence of a base, if necessary. The base may be the same ones as disclosed in the above Process (a), but an excess amount of the compound (V) may be used instead of a base. The reaction temperature varies according to the kinds of the reactive derivative of compound (IV) to be used, but it is usually in the range of about −30° C. to about 250° C., preferably in the range of about −10° C. to about 150° C.

The compound of the formula (V) may be prepared by the method disclosed in the following Chart 1.

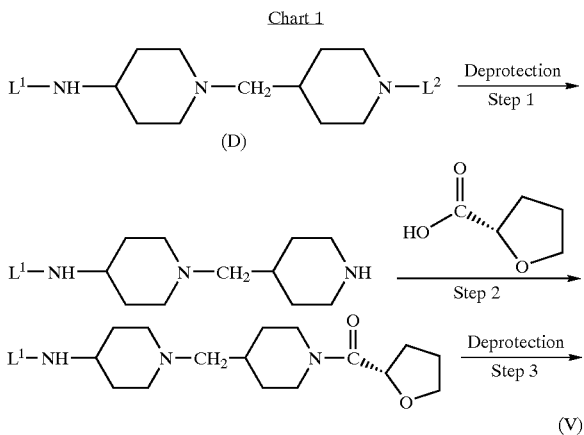

Chart 1 wherein $L^1$ and $L^2$ are protecting groups.

Step 2 in the above Chart 1 is carried out in the same manner as in the above Process (a), and Step 1 and Step 3 therein are carried out in the same manner as in the process of the removal of protecting group as mentioned below.

Removal of Protecting Group:

In Chart 1, the protecting groups represented by $L^1$ and $L^2$ may be any protecting groups being able to be removed by hydrolysis or hydrogenolysis. The protecting group being able to be removed by hydrolysis includes, for example, ethoxycarbonyl group, t-butoxy-carbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, etc., and the protecting group being able to be removed by hydrogeno-lysis includes, for example, benzyloxycarbonyl group, 3- or 4-chlorobenzyloxycarbonyl group, benzylsulfonyl group, etc.

The deprotection by hydrolysis is carried out by a conventional method, for example, in a suitable solvent under water-soluble inorganic or organic acidic or basic aqueous conditions, or under organic acidic conditions in a suitable solvent. The solvent includes, for example, aromatic hydrocarbons (e.g., benzene, toluene, xylene, etc.), ethers (e.g., diethyl ether, tetrahydrofuran, dioxane, etc.), halogenated hydrocarbons (e.g., methylene chloride, chloroform, etc.), ketones (e.g., acetone, methyl ethyl ketone, etc.), alcohols (e.g., methanol, ethanol, isopropanol, etc.), ethyl acetate, acetonitrile, water, and a mixture of these solvents. The acid includes, for example, inorganic acids (e.g., hydrochloric acid, hydrobromic acid, hydroiodic acid, sulfuric acid), and organic acids (e.g., formic acid, acetic acid, trifluoroacetic acid, p-toluenesulfonic acid, methanesulfonic acid, oxalic acid, etc.). The base includes, for example, an alkali metal hydroxide (e.g., sodium hydroxide, potassium hydroxide), and an alkali metal carbonate (e.g., sodium carbonate, potassium carbonate). The reaction is usually carried out at a temperature of from about 0° C. to about 150° C.

The deprotection by hydrogenolysis is carried out by a conventional method, for example, by reacting in the presence of a catalyst (e.g., palladium-on-carbon, Raney-nickel, etc.), and hydrogen gas or a hydrogen donor (e.g., ammonium formate, cyclohexene, etc.) in a suitable solvent. The solvent includes, for example, alcohols (e.g., ethanol, methanol), water, acetic acid, dioxane, tetrahydrofuran, ethyl acetate, and dimethylformamide. The reaction is usually carried out at a temperature of from about 0° C. to about 80° C., under atmospheric pressure or under pressure.

When $L^1$ and $L^2$ being able to be removed by hydrolysis are used as a protecting group, they should be selected as ones to be removed under different conditions.

The desired compound obtained in the above Processes can be isolated and purified by a conventional method such as chromato-graphy, recrystallization, re-precipitation, etc.

The compound (I) can be obtained either in the form of a free base or in the form of an acid addition salt thereof, according to the kinds of reaction conditions. The acid addition salt can be converted into a free base by a conventional method, for example, by treating it with a base such as alkali metal carbonate, an alkali metal hydroxide. On the other hand, the compound (I) in the form of a free base can be converted into an acid addition salt thereof by treating it with various acids in a conventional manner.

The test results on the pharmacological activities of the present compound are shown as follows.

Test Compounds:
  (1) Present Compound
    Compound 2 (Compound of Example 2): (S)-4-amino-5-chloro-2-methoxy-N-[1-[1-(2-tetrahydrofurylcarbonyl)-4-piperidinylmethyl]-4-piperidinyl]benzamide.fumarate
  (2) Reference Compound
    Compound R (Compound of Reference Example 2): (R)-4-amino-5-chloro-2-methoxy-N-[1-[1-(2-tetrahydrofurylcarbonyl)-4-piperidinyl-methyl]-4-piperidinyl]benzamide.fumarate (an enantiomer of Compound 2)
    Compound A: 4-amino-5-chloro-2-methoxy-N-[1-[1-(4-tetrahydropyranylcarbonyl)-4-piperidinylmethyl]-4-piperidinyl]benzamide.fumarate.1/4 hydrate (Compound of Example 5 of JP-A-2000–80081), M.p. 235–237° C. (recrystallized from ethanol)
    Compound B: 4-amino-5-chloro-N-[1-[1-(2-furoyl)-4-piperidinyl-methyl]-4-piperidinyl]-2-methoxybenzamide.fumarate.1/2 hydrate (Compound of Example 19 of JP-A-2000-80081), M.p. 179–181° C. (recrystallized from ethanol)
    Compound C (Compound of Reference Example 3): 4-amino-5-chloro-2-methoxy-N-[1-[1-(3-tetrahydrofurylcarbonyl)-4-piperidinyl-methyl]-4- piperidinyl]benzamide.fumarate (a racemic compound wherein the substitution position of tetrahydrofuran is different from the present compound)

(3) Gastrointestinal Motility Enhancer or Gastrointestinal Prokinetic Agent:

Cisapride: [Chemical name: cis-4-amino-5-chloro-N-[1-[3-(4-fluorophenoxy)propyl]-3-methoxy-4-piperidinyl]-2-methoxybenzamide; cf., Merck Index, 12 ed., 2377 (1996)]

Metoclopramide: [Chemical name: 4-amino-5-chloro-N-[2-(diethylamino)ethyl]-2-methoxybenzamide; cf., Merck Index, 12 ed., 6226 (1996)]

Experiment 1: Serotonin 4 (5-HT$_4$) Receptor Binding Assay

5-HT$_4$ receptor binding assay and the preparation of 5-HT$_4$ receptor membrane fractions therefor were carried out according to a modified method of the method of Grossman et al., British J. Pharmacol., 109, 618–624 (1993).

Std-Hartley guinea pigs weighing 300–400 g were decapitated, and the brain thereof was immediately taken out, and the striatum was dissected. To the tissue thus obtained was added 15-times volume of Hepes buffer (50 mM, pH7.4, 4° C.), and the mixture was homogenized in a Teflon homogenizer, and centrifuged at 48,000×g at 4° C. for 15 minutes. The pellet thus obtained was suspended in the same Hepes buffer in a volume of 1 ml per 30 mg of the wet tissues to give receptor membrane fractions.

In assay tubes, the Hepes buffer (50 mM. pH 7.4, 4° C., 1 ml) containing 0.1 nM [$^3$H]-GR113808 (GR113808: [1-[2-(methylsulfonyl-amino)ethyl]-4-piperidinyl]methyl 1-methylindole-3-carboxylate), the receptor membrane fraction, and either test compound or 30 µM serotonin was incubated at 37° C. for 30 minutes. The reaction was terminated by rapid vacuum filtration and washing with ice-cold 50 mM Tris-HCl buffer (pH 7.7, 3×4 ml) through Whatman GF/B filter paper using a Brandel cell harvester. Prior to the filtration, the filter to be used was presoaked in a 0.1% solution of polyethylenimine for one hour. The radioactivity on the filter was determined with ACS-II scintillation cocktail by a liquid scintillation counter.

The concentration of the test compounds causing 50% inhibition of specific binding of the [$^3$H]-GR113808 (IC$_{50}$ value) was determined by inhibitory rate of the test compound against the specific binding which was obtained by subtracting the non-specific binding from the total [$^3$H]-GR113808 binding. The results are shown in Table 1.

TABLE 1

| Serotonin 4 (5-HT$_4$) receptor binding activity | |
|---|---|
| Test Comp. | IC$_{50}$ (nM) |
| Compound 2* | 13.5 |
| Cisapride | 23.0 |

*The compound of Example 2

As is shown in Table 1, the IC$_{50}$ value of the present compound indicated that the present compound shows a more potent affinity for 5-HT$_4$ receptor than cisapride.

Experiment 2: Dopamine D$_2$ Receptor Binding Assay

Dopamine D$_2$ receptor binding assay and the preparation of receptor membrane fractions therefor were carried out according to a modified method of the method of Creese, I. et al., Eur. J. Pharmacol., 46, 337 (1977) and Peroutka, S. J. and Hamik, A., Eur. J. Pharmacol., 148, 297 (1988).

Crude synaptosome membrane fractions from rat brain was used as a receptor membrane fraction, and [$^3$H] spiperone (D$_2$) was used as a labeled ligand. A buffer (final volume: 1 ml) containing a receptor membrane fraction and a labelled ligand therefor was incubated for a prescribed period in the presence of a test compound in various concentrations, and the radioactive ligand binding to the receptor was separated on the filter paper using a cell harvester (manufactured by Brandel). The radioactivity on the filter was determined by a liquid scintillation counter, and the total binding of the ligand to the receptor was determined. On the other hand, the non-specific binding was determined in the presence of an excess amount of non-labeled ligand (spiperone (D$_2$)), and the specific binding was obtained by subtracting the non-specific binding from the total binding. The concentration of the test compound causing 50% inhibition of specific binding of the labeled ligand (IC$_{50}$ value) was determined by probit method. The results are shown in Table 2.

TABLE 2

| Dopamine D$_2$ receptor binding activity | |
|---|---|
| Test Comp. | IC$_{50}$ (nM) |
| Compound 2* | >10000 |
| Compound R | 948 |
| Metoclopramide | 480 |
| Cisapride | 390 |

*The compound of Example 2

In the dopamine D$_2$ receptor binding assay, the IC$_{50}$ value of the present compound is more than 10000 nM, which means that the present compound hardly shows affinity for dopamine D$_2$ receptor. On the other hand, the IC$_{50}$ value of the (R) optical isomer (Compound R), which is an enantiomer of Compound 2, is 948 nM, which means that Compound R shows an affinity for dopamine D$_2$ receptor although it is somewhat weaker than those of metoclopramide and cisapride.

Experiment 3: Assay on Defecation in Mice

Male mice of Std-ddY strain weighing 25–30 g were used. Free access to food and water was allowed up to the beginning of the procedure.

The mice (each group: five mice) were placed in a mesh bottom cage for fasting, and they were allowed for acclimation to the new environment for about one hour prior to the start of the experiment. A test compound, which was previously suspended in a 0.5% tragacanth solution, was administered orally to the mice. The fecal pellets were collected at 30, 60 and 120 minutes after the treatment of a test compound, and weighed.

The statistical judgment of efficacy was carried out between the control group (treated with a 0.5% tragacanth solution) and the test compound-treated group, and determined by Dunnett's test. The results are shown in Table 3.

TABLE 3

| Assay on defecation in mice | | |
|---|---|---|
| Test Comp. | Dosage (mg/kg) | Effect |
| Compound 2* | 1.0 | ++ |
|  | 3.0 | ++ |
| Compound R | 1.0 | ++ |
|  | 3.0 | ++ |
|  | 1.0 | − |
| Compound A | 3.0 | − |
|  | 10 | ++ |
|  | 1.0 | + |

TABLE 3-continued

Assay on defecation in mice

| Test Comp. | Dosage (mg/kg) | Effect |
|---|---|---|
| Compound B | 3.0 | + |
|  | 10 | ++ |
|  | 1.0 | + |
| Compound C | 3.0 | ++ |
|  | 3.0 | − |
| Cisapride | 30 | − |

*The compound of Example 2
−: Inactive
+: Moderately stimulated (P < 0.05)
++: Markedly stimulated (p < 0.01)

As is shown in Table 3, the present compound (Compound 2) showed a potent enhancing activity of defecation at a dose of either 1 mg/kg or 3.0 mg/kg. On the other hand, the compound of Example 5 of JP-A-2000-80081 (Compound A) showed no effects on defecation at both doses of 1.0 mg/kg and 3.0 mg/kg, and the compound of Example 19 of said publication (Compound B) showed an enhancing effect of defecation, but the effect thereof was weaker than that of Compound 2. Although Compound C (racemic compound), which is different from the present compound in the substitution position of the tetrahydrofuran ring, showed an enhancing effect on defecation at a dose of 3.0 mg/kg, it was not as strong as that of the present compound. In addition, cisapride did not show any enhancing effects on defecation at 3.0 mg/kg, and even at a high dose of 30 mg/kg.

Experiment 4: Gastrointestinal Motility Activity in Conscious Dog

Beagle dogs of a male were anesthetized with pentobarbital, and the abdominal cavity was opened, and force transducers (F-121S; manufactured by Star Medical Inc.) were sutured onto the seromuscular layer of the colon to make it possible to measure circular muscle contractions. Three or four force transducer were sutured onto in the colon from the lower part to the upper part at regular intervals. The lead wires from the transducers were brought out outside the body through a skin incision made between the scapulae, and were protected in a package of a jacket protector. The gastrointestinal motility activity was measured 2 or 3 weeks after the operation. The lead wires from the force transducers were connected with a telemeter system (DAS-800T: manufactured by Star Medical Inc.), and the gastrointestinal motility activity was analyzed by a personal computer system being connected therewith and recorded. A test compound was suspended in a 0.5% tragacanth solution, and administered via a cannula to be placed in the stomach to the dogs, which were one hour or more after feeding. The measurement was continued for 2 hours after the administration of test compounds.

The number of dogs showing Giant Migrating Contraction (GMC) and defecation within 2 hours after the administration of a test compound is indicated in Table 4.

TABLE 4

Gastrointestinal motility activity in dogs

| Test compound | Dosage (mg/kg) | Number to dogs which showed GMC[*3]/total number of dogs to be tested | Number of dogs which showed defecation/total number of dogs to be tested |
|---|---|---|---|
| Control[*2] |  | 0/5 | 0/5 |
|  | 0.03 | 1/4 | 1/4 |
| Compound 2[*1] | 0.1 | 3/5 | 2/5 |
|  | 0.3 | 4/5 | 3/5 |
| Cisapride | 10 | 1/7 | 1/7 |

[*1]The compound of Example 2
[*2]Control: 0.5% Tragacanth solution was administered.
[*3]GMC (Giant Migrating Contraction): Giant contraction wave migrating from the upper part of the colon to the lower part of the colon As is shown in Table 4, the present compound induced GMC at low doses of 0.1 mg/kg and 0.3 mg/kg in the gastrointestinal motility test on the dogs, and an enhancing effect of defecation was also observed. On the other hand, cisapride hardly shows effects of enhancing of defecation even at a high dose of 10 mg/kg.

Experiment 5: Effect on Electrocardiogram in Guinea Pigs (QTc: QT Interval Corrected for Heart Rate)

Male guinea pigs of Std-Hartley strain weighing 350–500 g were anesthetized with urethan (1.5 g/kg, ip). Under artificial respiration, a test compound was continuously infused intravenously to the guinea pigs for 15 minutes at a flow rate of 0.2 ml/kg/min., and the maximum dose was set at 30 mg/kg, and the QTc was calculated from the electrocardiogram by the following equation.

$$QTc = \frac{QT(second)}{\sqrt{RR(second)}}$$

QT (second): time from the beginning of Q-wave to the end of T-wave in electrocardiogram (usually, expressed by "second") [Expert Nurse, Vol. 3, No. 13, extra number of November, p. 19 (1987)]

RR (second): time from the peak of R-wave to the peak of the next R-wave in electrocardiogram (usually, expressed by "second").

The analysis of the electrocardiogram QTc was carried out by using Fluclet® 3.0 (manufactured by Dainippon Pharmaceutical Co., Ltd.), and the dose to be required to prolong the QTc intervals by 5% ($ED_{5\%}$) was calculated. The results are shown in Table 5.

TABLE 5

Effect on electrocardiogram in guinea pigs (QTc)

| Test compound | $ED_{5\%}$, iv (mg/kg) |
|---|---|
| Compound 2* | 24.9 |
| Compound R | 17.4 |
| Compound A | 16.9 |
| Compound B | 3.2 |
| Compound C | 9.4 |
| Cisapride | 0.3 |

*The compound of Example 2

Among the compounds showing a gastrointestinal motility enhancing activity (gastrointestinal prokinetic activity), certain benzamide-type compounds represented by cisapride have been known to disadvantageously affect the heart. Consequently, as an index for evaluating the effects on the heart, a dose to be required to prolong the QTc intervals by 5% of the electrocardiogram ($ED_{5\%}$) in guinea pigs was measured, which has widely been used.

As is shown in Table 5, the $ED_{5\%}$ value of cisapride for the QTc intervals of electrocardiogram in guinea pigs was quite low such as 0.3 mg/kg, and on the other hand, the $ED_{5\%}$ value of the present compound was high, i.e., 24.9 mg/kg, and from these results, the present compound can be considered to show quite few effects on the heart at a clinical dose.

On the other hand, the $ED_{5\%}$ value of the compound of Example 5 of JP-A-2000-80081 (Compound A) was comparatively high such as 16.9 mg/kg, but as is shown in Experiment 3 as mentioned above, the gastrointestinal motility enhancing activity of said compound was quite weak, and hence, this compound cannot satisfy the object of the present invention. Further, the $ED_{5\%}$ value of the compound of Example 19 of said publication (Compound B) was low such as 3.2 mg/kg, suggesting that Compound B has serious effects on the heart. In addition, Compound C, being different from the present compound only in the substitution position of the tetrahydrofuran ring, potently prolonged QTc intervals, although being not as strong as Compound B.

Experiment 6: Acute Toxicity

Male mice of Std-ddY strain weighing 25–30 g were used in a group of 5 or more animals. A test compound was suspended in physiological saline solution or a 1% lactose solution and administered intravenously to the mice. Then, the lethality of the mice was observed for 7 days after the treatment, and 50% lethal dose ($LD_{50}$) was determined. The $LD_{50}$ value of the present compound was more than 200 mg/kg.

As is shown in the results of the above pharmacological experiments 1 to 6, the present compound only showed the following good results.

(1) The present compound showed a more potent affinity for 5-$HT_4$ receptor being participated in gastrointestinal motility enhancing activity than cisapride.
(2) The present compound showed a remarkable enhancing activity of defecation in the mice by oral administration at a dose of 1.0 mg/kg.
(3) The present compound induced GMC in more than half of tested animals at a low dose of 0.1 mg/kg and further showed an enhancing activity of defecation in the gastrointestinal motility enhancing activity on dogs.
(4) The present compound showed a sufficiently large $ED_{5\%}$ value in the electrocardiogram test (QTc) in guinea pigs. That is, at a prospective clinical dose, the present compound can be considered to show few effects on the heart.
(5) The present compound showed the $IC_{50}$ value of more than 10000 nM in the dopamine $D_2$ binding assay, i.e., it showed a quite weak affinity for dopamine $D_2$ receptor. That is, it can be considered that the present compound shows no side effects with respect to the dopamine $D_2$ receptor antagonistic activity.
(6) The present compound can be considered not to have a problem with respect to toxicity because it has an $LD_{50}$ value of more than 200 mg/kg.

As is explained above, the present compound and a pharmaceutically acceptable acid addition salt thereof show (1) a potent affinity for 5-$HT_4$ receptor, (2) gastrointestinal motility enhancing effect such as enhancing activity of defecation by oral administration in the animal tests, (3) quite few effects on the heart, and (4) no antagonistic activity on dopamine $D_2$ receptor, which is a cause for side effects, and hence, the present compound and a pharmaceutically acceptable acid addition salt thereof can be used in the treatment or prophylaxis of gastrointestinal diseases or disorders as a selective 5-$HT_4$ receptor agonist. Especially, the present compound and a pharmaceutically acceptable acid addition salt thereof show an excellent motility enhancing activity for the lower gastrointestinal tract such as an enhancing activity of defecation, and hence, they can be used in the prophylaxis or treatment of gastrointestinal diseases such as irritable bowel syndrome, flaccid constipation, habitual constipation, drug-induced constipation (e.g., constipation induced by morphine, or a psychotropic), or as a pretreatment of endoscopy or X-ray examination by injection of barium into the colon, or in the treatment or prophylaxis of gastrointestinal diseases such as acute or chronic gastritis, reflux esophagitis, gastric or duodenal ulcer, gastric neurosis, paralytic ileus after surgery, senile ileus, postgastrectomy syndrome and intestinal pseudo-obstruction, as well as in the prophylaxis or treatment of anorexia, nausea, vomiting, abdominal fullness, upper abdominal discomfort, visceral pain, heartburn and eructation which are accompanied by the above mentioned gastrointestinal diseases, and diseases such as gastric or duodenal ulcer, scleroderma, diabetes, biliary duct disorders, etc. Moreover, the present compound and a pharmaceutically acceptable acid addition salt thereof can be used in the treatment or prophylaxis of central nervous diseases (e.g., schizophrenia, depression, memory disturbance, anxiety, etc.) or urinary diseases (e.g., urinary disturbances such as dysuria accompanied by urinary obstruction, prostatomegaly, etc.). Thus, the present compound and a pharmaceutically acceptable acid addition salt thereof can be used in the treatment or prophylaxis of various diseases, especially gastrointestinal dysfunction accompanied by the above-mentioned diseases, or especially the treatment, etc. of digestive diseases or various diseases as mentioned above, and hence, they are useful as a gastrointestinal motility enhancer (gastrointestinal prokinetic agent).

Especially, as shown in the above pharmacological experiments, the present compound shows a potent 5-$HT_4$ receptor agonistic activity and a potent enhancing activity of defecation without showing any antagonistic activity on dopamine $D_2$ receptor, which may cause side effects, and hence, the present compound shows an excellent usefulness such as quite few side effects on the heart.

The compound of the present invention can be administered either orally, parenterally or rectally. The dose of the compounds of the present invention varies according to the kinds of the compound, the administration routes, the conditions, ages of the patients, etc., but it is usually in the range of 0.01–5 mg/kg/day, preferably in the range of 0.05–1 mg/kg/day.

The compound of the present invention and a pharmaceutically acceptable acid addition salt thereof are usually administered in the form of a pharmaceutical preparation, which is prepared by mixing thereof with a pharmaceutically acceptable carrier or diluent. The pharmaceutically acceptable carrier or diluent may be any conventional ones being usually used in the pharmaceutical field, and do not react with the compound of the present invention. Suitable examples of the pharmaceutically acceptable carrier or diluent are, for example, lactose, inositol, glucose, mannitol, dextran, sorbitol, cyclodextrin, starch, partly pregelatinized starch, white sugar, magnesium metasilicate aluminate, synthetic aluminum silicate, crystalline cellulose, sodium carboxy-methylcellulose, hydroxypropyl starch, calcium carboxylmethyl cellulose, ion exchange resin, methylcellulose, gelatin, gum arabic, pullulan, hydroxypropyl cellulose, low substituted hydroxypropyl cellulose, hydroxypropylmethyl cellulose, polyvinylpyrrolidone, polyvinyl alcohol, alginic acid, sodium alginate, light anhydrous silicic acid, magnesium stearate, talc, tragacanth, bentonite, veegum, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, water, propyleneglycol, ethanol, sodium chloride, sodium hydroxide, hydrochloric acid, citric acid, benzyl alcohol, glutamic acid, glycine, methyl p-hydroxybenzoate, propyl p-hydroxy-benzoate, etc.

The pharmaceutical preparation is, for example, tablets, capsules, granules, powders, syrups, suspensions, injection preparations, suppositories, nasal drops, patches, sublingual preparations, etc. These preparations may be prepared by a conventional method. In the preparation of liquids, the compound of the present invention may be dissolved or suspended in water or a suitable other solvent, when administered. Tablets and granules may be coated by a conventional method.

These preparations may contain the compound of the present invention or a pharmaceutically acceptable acid addition salt thereof at a ratio of at least 0.01% by weight, preferably at a ratio of 0.1–70% by weight, based on the whole weight of the preparation. These preparations may also contain other therapeutically effective compounds as well.

The present invention is illustrated in more detail by the following Reference Examples and Examples, but should not be construed to be limited thereto. The identification of the compounds is carried out by Elemental analysis, Mass spectrum, IR spectrum, NMR spectrum, etc.

EXAMPLE A

Preparation of 4-Amino-1-[1-(2-tetrahydrofurylcarbonyl)-4-piperidinyl-methyl]piperidine (1) To a solution of 1-(1-benzyloxycarbonyl-4-piperidinylmethyl)-4-(t-butoxycarbonylamino)piperidine (10.0 g) in ethanol (100 ml) and water (10 ml) is added a 10% palladium-on-carbon (1.2 g), and the mixture is reduced at a room temperature under at a moderate pressure (3.0 kg/cm$^2$). After the consumption and disappearance of the starting compound is confirmed (about 2 hours thereafter), the catalyst is removed by filtration. The filtrate is evaporated under reduced pressure to give crude 4-(t-butoxycarbonylamino)-1-(4-piperidinyl-methyl)piperidine (about 7 g) as a white solid.

(2) A mixture of the above compound (3.2 g), (S)-tetrahydrofuran-2-carboxylic acid (1.4 g), 1-ethyl-3-(3-dimethylaminopropyl)carbodiimide hydrochloride (2.5 g), and chloroform (100 ml) is stirred at room temperature for 15 hours. The reaction solution is washed successively with a small amount of saturated aqueous sodium hydrogen carbonate solution and a small amount of saturated brine, and dried over anhydrous magnesium sulfate. The solvent is evaporated under reduced pressure, and the resulting oily product is purified by silica gel column chromatography (eluent; ethyl acetate: methanol=9:1) to give (S)-4-(t-butoxycarbonylamino)-1-[1-(2-tetrahydrofurylcarbonyl)-4-piperidinylmethyl]piperidine (2.1 g) as a solid.

(3) To a solution of the above product (2.1 g) in methylene chloride (50 ml) is added trifluoroacetic acid (3 ml), and the mixture is stirred at room temperature for 1 hour. The solvent and the excess amount of trifluoroacetic acid are concentrated to dryness under reduced pressure. Toluene is added to the residue, and the solvent is evaporated again under reduced pressure. Chloroform is added to the residue, and thereto is further added a small amount of 30% aqueous potassium carbonate solution, and the mixture is vigorously stirred at room temperature. The organic layer is separated, and the aqueous layer is extracted twice with chloroform. The organic layers are combined and dried over anhydrous magnesium sulfate. The solvent is evaporated under reduced pressure to give the desired compound (1.6 g) as an oily product.

EXAMPLE 1

Preparation of (S)-4-Amino-5-chloro-2-methoxy-N-[1-[1-(2-tetrahydrofurylcarbonyl)-4-pipeiridinylmethyl]-4-piperidinyl]benzamide (Compound 1)

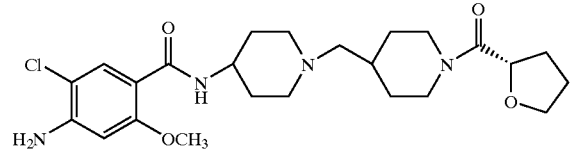

A mixture of (S)-tetrahydrofuran-2-carboxylic acid (7.4 g), 4-amino-5-chloro-2-methoxy-N-[1-(2-piperidinylmethyl)-4-piperidinyl]-benzamide (20 g), 1-ethyl-3-(3-dimethylaminopropyl)carbodiimide hydrochloride (13.1 g), and chloroform (200 ml) is stirred at room temperature overnight. The reaction solution is washed twice with an aqueous sodium hydrogen carbonate solution (50 ml), and dried over anhydrous magnesium sulfate. The solvent is evaporated under reduced pressure, and to the resulting residue is added ethyl acetate (50 ml), and the mixture is stirred at room temperature. The precipitated crystals are collected by filtration under reduced pressure, washed twice with a mixture of ethyl acetate and hexane (1:1, 30 ml), and dried to give the desired compound (Compound 1) (22.6 g).

M.p.: 146–148° C. (recrystallized from ethyl acetate); $^1$H-NMR (CDCl$_3$, δ ppm): 0.98–1.29 (2H, m), 1.44–1.7 (2H, m), 1.7–2.3 (14H, m), 2.59 (1H, m), 2.73 (2H, br-d, J=11.6 Hz), 3.01 (1H, m), 3.8–4.1 (5H, m), 3.89 (3H, s), 4.5–4.7 (2H, m), 6.29 (1H, s), 7.62 (1H, d, J=7.5 Hz), 8.10 (1H, s);

IR spectrum ($v_{max}$ cm$^{-1}$): 3385, 3317, 1639, 1591, 1537; Elemental analysis for C$_{24}$H$_{35}$ClN$_4$O$_4$· 0.25 H$_2$O; Calculated (%): C, 59.62; H, 7.40; N, 11.59; Cl, 7.33; Found (%): C, 59.86; H, 7.19; N,11.51; Cl, 7.31.

EXAMPLE 2

Preparation of (S)-4-Amino-5-chloro-2-methoxy-N-[1-[1-(2-tetrahydro-furylcarbonyl)-4-piperidinylmethyl]-4-piperidinyl]benzamide.fumarate (Compound 2)

To (S)-4-amino-5-chloro-2-methoxy-N-[1-[1-(2-tetrahydrofuryl-carbonyl)-4-piperidinylmethyl]-4-piperidinyl]benzamide (10.0 g) obtained in Example 1 is added ethanol (150 ml), and the mixture is stirred under heating at an outer temperature of about 60° C. To this solution is added fumaric acid (2.42 g), and the mixture is stirred at an outer temperature of about 80° C. for 3 hours. The mixture is allowed to cool to room temperature, and the precipitated crystals are collected by filtration under reduced pressure, washed twice with ethanol (30 ml), and dried to give the desired compound (Compound 2) (12.2 g).

M. p.: 232–235° C.

The compound thus obtained shows the retention time of 9.36 minutes in high-performance liquid chromatography (HPLC) under the following conditions, and the optical purity thereof is more than 99% ee (the retention time of the R-isomer is 11.45 minutes).

HPLC conditions: HPLC column: CHIRALPAK AS (manufactured by Daicel Chemical Industries, Ltd.); Inner diameter: 4.6 mm×250 mm; Mobile phase: hexane:ethanol:acetonitrile:diethylamine=70:22:8:0.4. Flow rate: 0.8 ml/min.; Column temperature: 30° C.; Wave length for detection: 280 nm; $^1$H-NMR (DMSO-$d_6$, δ ppm): 0.8–1.15 (2H, m), 1.45–1.7 (2H, m), 1.7–1.9 (6H, m), 1.9–2.1 (2H, m), 2.1–2.35 (4H, m), 2.4–2.6 (2H, m), 2.7–3.1 (3H, m), 3.88 (3H, s), 3.7–3.9 (3H, m), 3.97 (1H, br-d, J=12.5 Hz), 4.31 (1H, br-d, J=12.8 Hz), 4.63 (1H, t, J=6.5 Hz), 5.94 (2H, s, NH$_2$), 6.48 (1H, s), 6.60 (2H, s), 7.66 (1H, s), 7.73 (1H, d, J=7.5 Hz, CONH); IR spectrum ($v_{max}$ cm$^{-1}$): 3373, 1643, 1591, 1545; Elemental analysis for $C_{24}H_{35}ClN_4O_4 \cdot C_4H_4O_4$; Calculated (%): C, 56.51; H, 6.61; N, 9.41; Cl, 5.96; Found (%): C, 56.40; H, 6.50; N,9.39; Cl, 5.96;

EXAMPLE 3

Preparation of (S)-4-Amino-5-chloro-2-methoxy-N-[1-[1-(2-tetrahydro-furylcarbonyl)-4-piperidinylmethyl]-4-piperidinyl]benzamide.maleate (Compound 3)

To (S)-4-amino-5-chloro-2-methoxy-N-[1-[1-(2-tetrahydrofuryl-carbonyl)-4-piperidinylmethyl]-4-piperidinyl]benzamide (25 g) obtained in Example 1 is added ethanol (125 ml), and the mixture is stirred at room temperature. The compound is completely dissolved, and thereto is added maleic acid (6.66 g), and the mixture is stirred under heating at a bath temperature of 100° for 3 hours. The mixture is gradually cooled to room temperature, and the resulting crystals are collected by filtration, and washed twice with ethanol (30 ml). The crystals are dried to give crude crystals containing ethanol (29 g). To the crude crystals (21.4 g) are added ethanol (86 ml) and water (8.6 ml), and the mixture is stirred under heating at a bath temperature of 100° C. After the crystals are completely dissolved, the mixture is gradually allowed to cool to room temperature. The precipitated crystals are collected by filtration, washed twice with ethanol (30 ml), and dried to give the desired compound (Compound 3) (18 g).

M. p.: 232–235° C.; Elemental analysis for $C_{24}H_{35}ClN_4O_4 \cdot C_4H_4O_4$; Calculated (%): C, 56.51; H,6.61; N,9.41; Cl, 5.96; Found (%): C, 56.36; H,6.71; N,9.43; Cl, 5.71.

REFERENCE EXAMPLE 1

Preparation of 4-Amino-5-chloro-2-methoxy-N-[1-[1-(2-tetrahydro-furylcarbonyl)-4-piperidinylmethyl]-4-piperidinyl] benzamide.fumarate (Compound RS)

The desired compound (Compound RS) is obtained in a similar manner as in Example 1 and Example 2 except that tetrahydrofuran-2-carboxylic acid is used instead of (S)-tetrahydrofuran-2-carboxylic acid in Example 1.

M.p.: 229–234° C. (recrystallized from ethanol).

REFERENCE EXAMPLE 2

Preparation of (R)-4-Amino-5-chloro-2-methoxy-N-[1-[1-(2-tetrahydro-furylcarbonyl)-4-piperidinylmethyl]-4-piperidinyl] benzamide.fumarate (Compound R)

The desired compound (Compound R) is obtained in a similar manner as in Example 1 and Example 2 except that (R)-tetrahydro-furan-2-carboxylic acid is used instead of (S)-tetrahydrofuran-2-carboxylic acid in Example 1.

M.p.: 228–230° C. (recrystallized from ethanol).

REFERENCE EXAMPLE 3

Preparation of 4-Amino-5-chloro-2-methoxy-N-[1-[1-(3-tetrahydrofuryl-carbonyl)-4-piperidinylmethyl]-4-piperidinyl]benzamide (Compound C)

The desired compound (Compound C) is obtained in a similar manner as in Example 1 except that tetrahydrofuran-3-carboxylic acid is used instead of (S)-tetrahydrofuran-2-carboxylic acid in Example 1.

M. p.: 179–180° C. (recrystallized from ethyl acetate).

| Preparation 1: Preparation of tablets | |
|---|---|
| (S)-4-amino-5-chloro-2-methoxy-N-[1-[1-(2-tetrahydrofurylcarbonyl)-4-piperidinylmethyl]-4-piperidinyl]benzamide.fumarate (Compound 2) | 5 g |
| Lactose | 80 g |
| Corn starch | 30 g |
| Crystalline cellulose | 25 g |
| Hydroxypropyl cellulose | 3 g |

The above components are mixed and granulated in a conventional manner, and thereto are added light anhydrous silicic acid (0.7 g) and magnesium stearate (1.3 g). The mixture is further tabletted to give 1,000 tablets (each 145 mg).

| Preparation 2: Preparation of capsules | |
|---|---|
| (S)-4-amino-5-chloro-2-methoxy-N-[1-[1-(2-tetrahydrofurylcarbonyl)-4-piperidinylmethyl]-4-piperidinyl]benzamide.fumarate (Compound 2) | 5 g |
| Lactose | 165 g |
| Corn starch | 22 g |
| Hydroxypropyl cellulose | 3.5 g |
| Light silicic acid | 1.8 g |
| Magnesium stearate | 2.7 g |

The above components are mixed and granulated in a conventional manner, and the mixture is packed into a capsule to give 1,000 capsules.

| Preparation 3: Preparation of powder | |
|---|---|
| (S)-4-amino-5-chloro-2-methoxy-N-[1-[1-(2-tetrahydrofurylcarbonyl)-4-piperidinylmethyl]-4-piperidinyl]benzamide.fumarate (Compound 2) | 10 g |
| Lactose | 960 g |
| Hydroxypropyl cellulose | 25 g |
| Light silicic acid | 5 g |

The above components are mixed by a conventional manner to give a powder preparation.

| Preparation 4: Preparation of injection (amount for 1000 ampoules) | |
|---|---:|
| (S)-4-amino-5-chloro-2-methoxy-N-[1-[1-(2-tetrahydrofurylcarbonyl)-4-piperidinylmethyl]-4-piperidinyl]benzamide.fumarate (Compound 2) | 2 g |
| Sorbitol | 100 g |
| Distilled water for injection | q.s. |
| Total | 2000 ml |

(S)-4-Amino-5-chloro-2-methoxy-N-[1-[1-(2-tetrahydrofuryl-carbonyl)-4-piperidinylmethyl]-4-piperidinyl]benzamide.fumarate (Compound 2) and sorbitol are dissolved in a part of distilled water for injection, and thereto is added a remaining portion of distilled water for injection to adjust the total volume of the mixture. The solution thus obtained is filtered through a membrane filter (0.22 μm), and each 2 ml of the filtrate is filled into ampoules, which are further sterilized at 121° C. for 20 minutes.

INDUSTRIAL APPLICABILITY

The compound (I) of the present invention and a pharmaceutically acceptable acid addition salt thereof show not only a potent affinity for 5-HT$_4$ receptor and a potent enhancing activity of defecation, but show quite weak side effects, for example, no antagonistic activity on dopamine D$_2$ receptor and few effects on the heart, and hence, they can be useful in the prophylaxis or treatment of various diseases such as gastrointestinal diseases (e.g., irritable bowel syndrome, flaccid constipation, habitual constipation, drug-induced constipation (e.g., constipation induced by morphine, a psychotropic), etc.), central nervous diseases (e.g., schizophrenia, depression, disturbance of memory, anxiety, etc.), and urinary diseases (e.g., urinary disturbances such as dysuria accompanied by urinary obstruction or prostatomegaly), or various gastrointestinal dysfunctions (e.g., anorexia, nausea, vomiting, abdominal fullness, etc.) accompanied by the treatment of various diseases as mentioned above. Therefore, they are useful especially as a gastrointestinal motility enhancer or a gastrointestinal prokinetic agent. In addition, the compound of the formula (III) is useful as an intermediate for preparing the compound of the formula (I).

What is claimed is:

1. An (S)-4-amino-5-chloro-2-methoxy-N-[1-[1-(2-tetrahydrofurylcarbonyl)-4piperidinylmethyl]-4-piperidinyl]benzamide of the following formula (I):

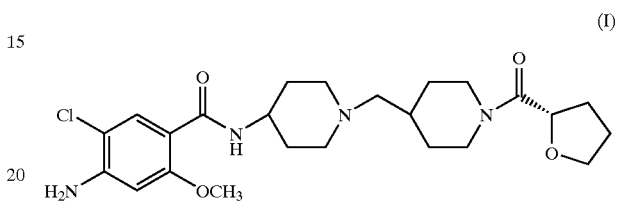

or a pharmaceutically acceptable acid addition salt thereof, or a hydrate thereof.

2. An (S)-4-amino-5-chloro-2-methoxy-N-[1-[1-(2-tetrahydrofurylcarbonyl)-4-piperidinylmethyl]-4-piperidinyl]benzamide.fumarate or a hydrate thereof.

3. An (S)-4-amino-5-chloro-2-methoxy-N-[1-[1-(2-tetrahydrofurylcarbonyl)-4-piperidinylmethyl]-4-piperidinyl]benzamide.maleate, or a hydrate thereof.

4. A pharmaceutical composition, which comprises as an active ingredient an (S)-4-amino-5-chloro-2-methoxy-N-[1-[1-(2-tetrahydrofurylcarbonyl)-piperidinylmethyl]-4-piperidinyl]benzamide, or a pharmaceutically acceptable acid addition salt thereof, or a hydrate thereof in admixture with a pharmaceutically acceptable carrier or diluent.

* * * * *

UNITED STATES PATENT AND TRADEMARK OFFICE
CERTIFICATE OF CORRECTION

PATENT NO.   : 6,696,468 B2
DATED        : February 24, 2004
INVENTOR(S)  : Shiro Kato et al.

It is certified that error appears in the above-identified patent and that said Letters Patent is hereby corrected as shown below:

Column 2,
Line 42, please change "R'''" to -- $R^{10}$ --.

Column 20,
Line 27, please change "benzarnide" to -- benzamide --.

Signed and Sealed this

Fifteenth Day of March, 2005

JON W. DUDAS
*Director of the United States Patent and Trademark Office*